(12) United States Patent
Orebaugh et al.

(10) Patent No.: US 9,743,616 B1
(45) Date of Patent: Aug. 29, 2017

(54) INBRED CORN LINE I10516

(71) Applicant: BECK'S SUPERIOR HYBRIDS, Atlanta, IN (US)

(72) Inventors: Benjamin Earl Orebaugh, Fishers, IN (US); Kevin James Cavanaugh, Arcadia, IN (US); George Keith Rufener, II, Cicero, IN (US)

(73) Assignee: Beck's Superior Hybrids, Inc., Atlanta, IN (US)

( * ) Notice: Subject to any disclaimer, the term of this patent is extended or adjusted under 35 U.S.C. 154(b) by 0 days.

(21) Appl. No.: 15/092,881

(22) Filed: Apr. 7, 2016

(51) Int. Cl.
*A01H 5/00* (2006.01)
*C12N 15/82* (2006.01)
*A01H 5/10* (2006.01)
*A01H 1/02* (2006.01)

(52) U.S. Cl.
CPC ............ *A01H 5/10* (2013.01); *A01H 1/02* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 6,025,547 A | 2/2000 | Stucker | |
| 6,096,953 A | 8/2000 | Hoffbeck | |
| 7,635,808 B1 * | 12/2009 | Maves | A01H 5/10 435/412 |

OTHER PUBLICATIONS

Allard, 1960, Principles of Plant Breeding, John Wiley & Sons, Inc., p. 55.
Darnell, et al., 1990, DNA Replication, Repair and Recombination, Molecular Cell Biology, 2nd Edition, W. H. Freeman and Company, p. 478.
Eshed, et al., 1996, Less-than-additive epistatic interactions of quantitative trait loci in tomato, Genetics, 143:1807-1817.
Kraft, et al., 2000, Linkage disequilibrium and fingerprinting in sugar beet, Theor. Appl. Genet., 101:323-326.
Murray, et al., 1988, Restriction fragment length polymorphisms: What are they and how can breeders use them? Proceedings of the 43rd Annual Corn and Sorghum Industry Research Conference, 43:72-87.
Napoli, et al., 1990, Introduction of a chimeric chalcone synthase gene into petunia results in reversible co-suppression of homologous genes in trans, The Plant Cell, 2:279-289.
Phillips, et al., Corn and Corn Improvement, ASA Monograph No. 18, 3rd Edition, p. 358.

* cited by examiner

*Primary Examiner* — Vinod Kumar
(74) *Attorney, Agent, or Firm* — Jondle & Associates, P.C.

(57) ABSTRACT

An inbred corn line designated I10516 is disclosed. The invention relates to the plants and seeds of inbred corn line I10516 and methods for producing a corn plant produced by crossing the inbred corn line I10516 with itself or with another corn plant. The invention also relates to methods for producing a corn plant containing in its genetic material one or more transgenes and to the transgenic corn plants and plant parts produced by those methods. The invention also relates to corn cultivars and plant parts derived from inbred corn line I10516 and to methods for producing other corn cultivars, lines, or plant parts derived from inbred corn line I10516, and to the corn plants and parts derived from use of those methods. The invention further relates to hybrid corn seeds, plants, and plant parts produced by crossing inbred corn line I10516 with another corn cultivar.

21 Claims, No Drawings

INBRED CORN LINE I10516

BACKGROUND OF THE INVENTION

This present invention relates to a new and distinctive inbred dent corn line designated I10516. All publications cited in this application are herein incorporated by reference.

The goal of plant breeding is to combine in a single variety or hybrid various desirable traits. For vegetable crops, such as sweet corn, these traits may include resistance to diseases and insects, tolerance to heat and drought, reducing the time to crop maturity, greater yield, better agronomic quality, processing traits, such as high processing plant recovery, tender kernels, pleasing taste, uniform kernel size and color, attractive husk package and husked ears, ability to ship long distances, ease of mechanical or manual harvest, tipfill, row straight. With mechanical harvesting of many crops, uniformity of plant characteristics such as germination and stand establishment, growth rate, maturity, and plant and ear height, is important.

Corn (Zea mays L., also called maize) is the most valuable crop grown in the United States. Along with wheat, rice, and potatoes, corn ranks as one of the four most important crops in the world. Three major types of corn are grown in the United States: 1) grain or field corn; 2) sweet corn; and 3) popcorn. Grain or field corn is grown annually for grain on from 55 to 60 million acres, with seed production in excess of 4 billion bushels, and in addition, around 8 million acres of this type are harvested for silage. Grain corn is further classified commercially into four main types: 1) dent corn; 2) flint corn; 3) flour or soft corn; and 4) waxy corn.

Dent corn is a particular type of grain corn. Dent corn is the most common type of corn, comprising about 90 percent of the corn grown in the United States. Dent corn, when fully ripe, has a pronounced depression or dent at the crown of the kernels. The kernels contain a hard form of starch at the sides and a soft type of starch in the center. This latter starch shrinks as the kernel ripens resulting in the terminal depression. Dent varieties vary in kernel shape from long and narrow to wide and shallow. Farmers harvest dent corn when the seeds become hard and ripe. Dent corn is primarily used as a livestock feed, but can also be used to make many food and industrial products. Dent corn is grown in all parts of the United States Corn Belt.

The foregoing examples of the related art and limitations related therewith are intended to be illustrative and not exclusive. Other limitations of the related art will become apparent to those of skill in the art upon a reading of the specification.

SUMMARY OF THE INVENTION

According to the invention, there is provided a novel inbred dent corn, Zea mays L., line, designated I10516 and processes for making I10516. This invention relates to seed of inbred corn line I10516, to the plants of inbred corn line I10516, to plant parts of inbred corn line I10516, and to processes for making a corn plant that comprise crossing inbred corn line I10516 with another corn plant. This invention also relates to processes for making a corn plant containing in its genetic material one or more traits introgressed into inbred corn line I10516 through backcross conversion and/or transformation, and to the corn seed, plant and plant parts produced thereby. This invention also relates to a hybrid corn seed, plant or plant part produced by crossing inbred corn line I10516 or a locus conversion of inbred corn line I10516 with another corn variety. The invention further relates to a method of producing a corn product with inbred corn line I10516 and to the corn product produced by the method.

DETAILED DESCRIPTION OF THE INVENTION

In the description and tables that follow, a number of terms are used. In order to provide a clear and consistent understanding of the specification and claims, including the scope to be given such terms, the following definitions are provided:

Abiotic stress tolerance. Resistance to non-biological sources of stress conferred by traits such as nitrogen utilization efficiency, altered nitrogen responsiveness, drought resistance, cold and salt resistance.

Allele. The allele is any of one or more alternative form of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Amylose. A polysaccharide made up of $\alpha(1\rightarrow 4)$ glycosidic bonds. Amylose is one of the two components of starch; the other component is amylopectin. High amylose starch, amylomaize, is cultivated for the use of its gel strength and for use as a resistant starch in food products.

Anthesis. The time of a flower's opening.

Antioxidant. A chemical compound or substance that inhibits oxidation, including but not limited to tocopherol or tocotrienols.

Backcrossing. Backcrossing is a process in which a breeder repeatedly crosses hybrid progeny back to one of the parental genotypes one or more times.

Backcross progeny. Progeny plants produced by crossing inbred corn line I10516 with plants of another corn line that comprise a desired trait or locus, selecting F1 progeny plants that comprise the desired trait or locus, and crossing the selected F1 progeny plants with the inbred corn line I10516 plants one or more times to produce backcross progeny plants that comprise said trait or locus.

Breeding. The genetic manipulation of living organisms.

Breeding cross. A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed.

Breeding value. A relative value determined by evaluating the progeny of the parent. For corn the progeny is often the F1 generation and the parent is often an inbred variety.

Carbohydrate. Organic compounds comprising carbon, oxygen and hydrogen, including sugars, starches and cellulose.

Cell. Cell as used herein includes a plant cell, whether isolated, in tissue culture or incorporated in a plant or plant part.

Collection of seeds. In the context of the present invention a collection of seeds will be a grouping of seeds mainly containing similar kinds of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

Cross-pollination. Fertilization by the union of two gametes from different plants.

D and D1-Dn. Represents the generation of doubled haploid.

Daily heat unit value. The daily heat unit value is calculated as follows: (the maximum daily temperature+the minimum daily temperature)/2 minus 50. All temperatures are in degrees Fahrenheit. The maximum temperature threshold is 86 degrees, if temperatures exceed this, 86 is used. The minimum temperature threshold is 50 degrees, if temperatures go below this, 50 is used.

Dent corn. Botanically known as *Zea mays* var. *indentata*. A tall-growing variety of corn having yellow or white kernels that are indented at the tip.

Digestible energy. Near-infrared transmission spectroscopy, NIT, prediction of digestible energy.

Diploid plant part. Refers to a plant part or cell that has the same diploid genotype as inbred corn line I10516.

Dropped ears. Ears that have fallen from the plant to the ground.

Dry down. This is the rate at which a hybrid will reach acceptable harvest moisture Ear cob diameter. The average diameter of the cob measured at the midpoint.

Ear diameter. The average diameter of the ear at its midpoint.

Ear height. The ear height is a measure from the ground to the upper ear node attachment, and is measured in centimeters or inches.

Ear length. The average length of the ear.

Ear shank length. The average length of the ear shank.

Ear taper (shape). The taper or shape of the ear scored as 1=slight, 2=average, and 3=extreme.

Ear weight. The average weight of an ear.

Emasculate. The removal of plant male sex organs or the inactivation of the organs with a chemical agent or a cytoplasmic or nuclear genetic factor conferring male sterility.

Endosperm type. Endosperm type refers to endosperm genes and types such as starch, sugary alleles (su1, su2, etc.), sugary enhancer or extender, waxy, amylose extender, dull, brittle alleles (bt1, bt2, etc.) other sh2 alleles, and any combination of these.

Essential amino acids. Amino acids that cannot be synthesized by an organism and therefore must be supplied in the diet.

Essentially all the physiological and morphological characteristics. A plant having essentially all the physiological and morphological characteristics means a plant having the physiological and morphological characteristics, except for the characteristics derived from the converted gene.

Expressing. Having the genetic potential such that under the right conditions, the phenotypic trait is present.

Fatty acid. A carboxylic acid (or organic acid), often with a long aliphatic tail (long chains), either saturated or unsaturated.

F1 progeny. A progeny plant produced by crossing a plant of one corn with a plant or another corn line.

GDUs. Growing degree units which are calculated by the Barger Method, where the heat units for a 24 hour period are calculated as GDUs=[(Maximum daily temperature+Minimum daily temperature)/2]−50. The highest maximum daily temperature used is 86° F. and the lowest minimum temperature used is 50° F.

GDUs to shed. The number of growing degree units (GDUs) or heat units required for a variety to have approximately 50% of the plants shedding pollen as measured from time of planting. GDUs to shed is determined by summing the individual GDU daily values from planting date to the date of 50% pollen shed.

GDUs to silk. The number of growing degree units for a variety to have approximately 50% of the plants with silk emergence as measured from time of planting. GDUs to silk is determined by summing the individual GDU daily values from planting date to the date of 50% silking.

Gene silencing. The interruption or suppression of the expression of a gene at the level of transcription or translation.

Genotype. Refers to the genetic make-up or profile of a cell or organism.

Haploid plant part. Refers to a plant part or cell that has a haploid genotype.

H and H1. Refers to the haploid generation.

Herbicide resistant or tolerant. A plant containing any herbicide-resistant gene or any DNA molecule or construct (or replicate thereof) which is not naturally occurring in the plant which results in increase tolerance to any herbicide including, imidazoline, sulfonylurea, glyphosate, glufosinate, L-phosphinothricin, triazine and benzonitrile. For purposes of this definition, a DNA molecule or construct shall be considered to be naturally occurring if it exists in a plant at a high enough frequency to provide herbicide resistance without further selection and/or if it has not been produced as a result of tissue culture selection, mutagenesis, genetic engineering using recombinant DNA techniques or other in vitro or in vivo modification to the plant.

HTU. HTU is the summation of the daily heat unit value calculated from planting to harvest.

Hybrid variety. A substantially heterozygous hybrid line and minor genetic modifications thereof that retain the overall genetics of the hybrid line including but not limited to a locus conversion, a mutation, or a somoclonal variant.

Inbred. A variety or line developed through inbreeding or doubled haploidy that preferably comprises homozygous alleles at about 95% or more of its loci. An inbred can be reproduced by selfing or growing in isolation so that the plants can only pollinate with the same inbred variety.

Inbreeding depression. The inbreeding depression is the loss of performance of the inbreds due to the effect of inbreeding, i.e. due to the mating of relatives or to self-pollination. It increases the homozygous recessive alleles leading to plants which are weaker and smaller and having other less desirable traits.

Introgression. The process of transferring genetic material from one genotype to another.

Kernel aleurone color. The color of the aleurone scored as white, pink, tan, brown, bronze, red, purple, pale purple, colorless, or variegated.

Kernel length. The average distance from the cap of the kernel to the pedicel.

Linkage. Refers to a phenomenon wherein alleles on the same chromosome tend to segregate together more often than expected by chance if their transmission was independent.

Linkage disequilibrium. Refers to a phenomenon wherein alleles tend to remain together in linkage groups when segregating from parents to offspring, with a greater frequency than expected from their individual frequencies.

Locus. A specific location on a chromosome.

Locus conversion (also called a 'trait conversion'). A locus conversion refers to plants within a variety or line that have been modified in a manner that retains the overall genetics of the variety and further comprises one or more loci with a specific desired trait, such as male sterility, insect control, disease control or herbicide tolerance. Examples of single locus conversions include mutant genes, transgenes and native traits finely mapped to a single locus. One or more locus conversion traits may be introduced into a single corn variety or line.

Male sterility. A male sterile plant is one which produces no viable pollen (pollen that is able to fertilize the egg to produce a viable seed). Male sterility prevents self-pollination. These male sterile plants are therefore useful in hybrid plant production.

Moisture. The moisture is the actual percentage moisture of the grain at harvest.

Nucleic acid. An acidic, chainlike biological macro-molecule consisting of multiple repeat units of phosphoric acid, sugar, and purine and pyrimidine bases.

Percent identity. Percent identity as used herein refers to the comparison of the alleles present in two varieties. For example, when comparing two inbred plants to each other, each inbred plant will have the same allele (and therefore be homozygous) at almost all of their loci. Percent identity is determined by comparing a statistically significant number of the homozygous alleles of two varieties. For example, a percent identity of 90% between inbred corn line I10516 and another variety means that the two varieties have the same homozygous alleles at 90% of their loci.

Plant. As used herein, the term "plant" includes reference to an immature or mature whole plant, including a plant that has been detasseled or from which seed or grain has been removed. Seed or embryo that will produce the plant is also considered to be the plant.

Plant cell. Plant cell, as used herein includes plant cells whether isolated, in tissue culture, or incorporated in a plant or plant part.

Plant habit. This is a visual assessment assigned during the late vegetative to early reproductive stages to characterize the plants leaf habit. It ranges from decumbent with leaves growing horizontally from the stalk to a very upright leaf habit, with leaves growing near vertically from the stalk.

Plant height. This is a measure of the height of the plant from the ground to the tip of the tassel, and is measured in centimeters or inches.

Plant intactness. This is a visual assessment assigned to a hybrid or inbred at or close to harvest to indicate the degree that the plant has suffered disintegration through the growing season. Plants are rated from 1 (poorest) to 9 (best) with poorer scores given for plants that have more of their leaf blades missing.

Plant part. As used herein, the term "plant part" includes leaves, stems, roots, seeds, grain, embryo, pollen, ovules, flowers, ears, cobs, husks, stalks, root tips, anthers, pericarp, silk, tissue, cells and the like.

Platform. Indicates the variety with the base genetics and the variety with the base genetics comprising locus conversion(s). There can be a platform for the inbred corn line and the hybrid corn variety.

Pollen shed. This is a visual rating assigned at flowering to describe the abundance of pollen produced by the anthers. Inbreds are rated 1 (poorest) to 9 (best) with the best scores for inbreds with tassels that shed more pollen during anthesis.

Post-anthesis root lodging. This is a percentage plants that root lodge after anthesis: plants that lean from the vertical axis at an approximately 30° angle or greater.

Pre-anthesis brittle snapping. This is a percentage of "snapped" plants following severe winds prior to anthesis Pre-anthesis root lodging. This is a percentage plants that root lodge prior to anthesis: plants that lean from the vertical axis at an approximately 30° angle or greater.

Quantitative Trait Loci (QTL). Quantitative trait loci refer to genetic loci that control to some degree numerically representable traits that are usually continuously distributed.

Regeneration. Regeneration refers to the development of a plant from tissue culture.

Resistance. Synonymous with tolerance. The ability of a plant to withstand exposure to an insect, disease, herbicide or other condition. A resistant plant variety will have a level of resistance higher than a comparable wild-type variety.

Root Lodging. The root lodging is the percentage of plants that root lodge (i.e., those that lean from the vertical axis at an approximate 300 angle or greater would be counted as root lodged).

Seed. Fertilized and ripened ovule, consisting of the plant embryo, varying amounts of stored food material, and a protective outer seed coat. Synonymous with grain.

Seed quality. This is a visual rating assigned to the kernels of the inbred. Kernels are rated 1 (poorest) to 9 (best) with poorer scores given for kernels that are very soft and shriveled with splitting of the pericarp visible and better scores for fully formed kernels.

Seedling vigor. This is the vegetative growth after emergence at the seedling stage, approximately five leaves.

Self-pollination. A plant is self-pollinated if pollen from one flower is transferred to the same or another flower of the same plant.

Sib-pollination. A plant is sib-pollinated when individuals within the same family or variety are used for pollination.

Silking ability. This is a visual assessment given during flowering. Plants are rated on the amount and timing of silk production. Plants are rated from 1 (poorest) to 9 (best) with poorer scores given for plants that produce very little silks that are delayed past pollen shed.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Single-nucleotide polymorphism. A DNA sequence variation occurring when a single nucleotide in the genome differs between individual plants or plant varieties. The differences can be equated with different alleles, and indicate polymorphisms. A number of SNP markers can be used to determine a molecular profile of an individual plant or plant variety and can be used to compare similarities and differences among plants and plant varieties.

Site specific integration. Genes that create a site for site specific DNA integration. This includes the introduction of FRT sites that may be used in the FLP/FRT system and/or Lox sites that may be used in the Cre/Loxp system. For example, see Lyznik et al., Site-Specific Recombination for Genetic Engineering in Plants, Plant Cell Rep (2003) 21:925-932 and WO 99/25821.

SSRs. Genetic markers based on polymorphisms in repeated nucleotide sequences, such as microsatellites. A marker system based on SSRs can be highly informative in linkage analysis relative to other marker systems in that multiple alleles may be present.

Stalk lodging. This is the percentage of plants that stalk lodge, i.e., stalk breakage, as measured by either natural lodging or pushing the stalks and determining the percentage of plants that break off below the ear. This is a relative rating of an inbred to other inbreds, or a hybrid to other hybrids for standability.

Standability. A term referring to the how well a plant remains upright towards the end of the growing season. Plants with excessive stalk breakage and/or root lodging would be considered to have poor standability.

Starch (or amylum). A carbohydrate consisting of a large number of glucose units joined by glycosidic bonds. Starch consists of two types of molecules: the linear and helical amylose and the branched amylopectin.

Stay Green. Stay green is the measure of plant health near the time of black layer formation (physiological maturity). A high score indicates better late-season plant health.

Tassel weight. The average weight of a tassel (in grams) just prior to pollen shed.

Tiller. A secondary shoot that has developed as a tassel capable of shedding pollen.

Transgene. A genetic sequence which has been introduced into the nuclear or chloroplast genome of a corn plant by a genetic transformation technique.

Variety. A corn line and minor genetic modifications thereof that retain the overall genetics of the line including but not limited to a locus conversion, a mutation, or a somoclonal variant.

Waxy starch. Some cultivated plants have pure amylopectin starch without amylose, known as waxy starches; the most used is waxy maize. The waxy characteristic is an example of a recessive trait.

Yield. The yield is the tons of green corn or green weight per acre. It can also be defined as the number of ears per acre or per plant.

Yield (Bushels/Acre). The yield is the actual yield of the grain at harvest adjusted to 15.5% moisture.

According to the invention, there is provided a novel inbred corn line, designated I10516. Inbred corn line I10516 was developed by traditional inbreeding of selected individuals over successive generations in a breeding program aimed at developing a breeding line with good agronomic characteristics, such as standability, disease resistance, seed yield and utility as a male in seed production. I10516 was selected based on a "per se" basis by evaluating its performance in hybrid combinations and selecting for grain yield, grain test weight, root and stalk strength. Inbred corn line I10516 is characterized by having a "red ring" at the point where the stalk meets the roots, and in many cases, this "red ring" carries over into hybrids containing 1105016 as a parent. I10516 has a very upright architecture in the top half of the plant, while the last 6-8 inches of the upper leaves droop over distinctly. Additionally, inbred corn line I10516 has a thick tassel main spike, and branches with very distinctive, upright tassel branches (2-3 branches).

The inbred has shown uniformity and stability as described in the following variety description information. It has been self-pollinated a sufficient number of generations with careful attention to plant type. The line has been increased with continued observation for uniformity. Inbred corn line I10516 has the following morphological and other characteristics based on data taken in Indiana in 2015.

Table 1

Variety Description Information

TYPE: Yellow dent corn
REGION WHERE DEVELOPED IN THE U.S.A.: Indiana
MATURITY: Planted May 7, 2015
From emergence to 50% of plants in silk:
  Days: 75
  Heat units: 1459
From emergence to 50% of plant in pollen:
  Days: 75
  Heat units: 1459
From 10% to 90% pollen shed:
  Days: 4
  Heat units: 90.6
PLANT:
Plant height (to tassel tip) (inches): 81.0
Ear height (to base of top ear node) (inches): 26.0
Length of top ear internode (inches): 6.75
Average number of tillers: 0
Average number of ears per stalk: 2
Anthocyanin of brace roots: None (green); however, there is a red ring at junction of roots and stalk
LEAF:
Width of ear node leaf (cm): 9.5
Length of ear node leaf (cm): 86.0
Number of leaves above top ear: 5
Degree leaf angle (from $2^{nd}$ leaf above ear at anthesis to stalk above leaf): 40
Leaf color: Light-medium green
Leaf sheath pubescence (1=none, 9=like peach fuzz): 1
Marginal waves (1=none, 9=many): 6
Longitudinal creases (1=none, 9=many): 2, very few
TASSEL:
Color: Green
Number of primary lateral branches: 4
Branch angle from central spike: 15°
Tassel length (from top leaf collar to tassel tip) (cm): 39.0
Pollen shed (0=male sterile, 9=heavy shed): 6
Anther color: Yellow
Glume color: Green
Bar glumes (1=absent, 2=present): 1
EAR:
Unhusked data:
  Silk color (3 days after emergence): Green/yellow
  Fresh husk color (25 days after 50% silking): Medium green
  Dry husk color (65 days after 50% silking): Light brown
  Position of ear at dry husk stage (1=upright, 2=horizontal, 3=pendent): 1
  Husk tightness (1=very loose, 9=very tight): 5
  Husk extension (at harvest) (1=short (ears exposed), 2=medium (<8 cm), 3=long (8-10 cm beyond ear tip), 4=very long (>10 cm)): 2
Husked ear data:
  Ear length (cm): 16.0
  Ear diameter at mid-point (inches): 1.75
  Ear weight (gm): 124.0
  Number of kernel rows: 16
  Kernel rows (1=indistinct, 2=distinct): 1
  Row alignment (1=straight, 2=slightly curved, 3=spiral): 2
  Shank length (cm): 2.5
  Ear taper (1=slight, 2=average, 3=extreme): 2

KERNEL (Dried):
Kernel length (mm): 11.0
Kernel width (mm): 10.0
Kernel thickness (mm): 5.0%
% Round kernels (shape grade): 40
Aleurone color pattern (1=homozygous, 2=segregating): 1
Aleurone color: Homozygous yellow
Hard endosperm color: Dark yellow
Endosperm type (1=sweet (su1), 2=extra sweet (sh2), 3=normal starch, 4=high amylose starch, 5=waxy starch, 6=high protein, 7=high lysine, 8=super sweet (se), 9=high oil, 10=other): 3
Weight per 100 kernels (unsized sample) (gm): 34.0
COB:
Cob diameter at mid-point (inches): 1.25
Cob color: Medium red
DISEASE RESISTANCE (1=most susceptible, 9=most resistant):
  Leaf blights, wilts, and local infection diseases:
    Common rust (*Puccinia sorghi*): 6
    Common smut (*Ustilago maydis*): 8
    Gray leaf spot (*Cercospora zeae-maydis*): 5
    Northern leaf blight (*Exserohilum turcicum*): 6
  Systemic diseases:
    Head smut (*Sphacelotheca reiliana*): 7
  Stalk rots:
    Anthracnose stalk rot (*Colletotrichum graminicola*): 7
    *Diplodia* stalk rot (*Stenocarpella maydis*): 7
    *Fusarium* stalk rot (*Fusarium moniliforme*): 7
    *Gibberella* stalk rot (*Gibberella zeae*): 7
INSECT/PEST RESISTANCE (1=most susceptible, 9=most resistant):
  Corn earworm (*Helicoverpa zea*):
    Leaf-feeding: 5
    Silk-feeding: 4
    Ear damage: 6
  European corn borer (*Ostrinia nubilalis*):
    $1^{st}$ generation (typically whorl leaf feeding): 6
    $2^{nd}$ generation (typically leaf sheath-collar feeding): 4
  Fall armyworm (*Spodoptera frugiperda*):
    Leaf-feeding: 4
    Silk-feeding: 6
  Two-spotted spider mite (*Tetranychus urticae*): 4
AGRONOMIC TRAITS:
  Stay green (at 65 days after anthesis) (1=worst, 9=excellent): 5
  Percent dropped ears at 65 days after anthesis: 0
  Percent pre-anthesis brittle snapping: 0
  Percent pre-anthesis root lodging: 0
  Percent post-anthesis root lodging: 0

Further Embodiments of Invention

Dent corn is an important and valuable vegetable crop. Thus, a continuing goal of plant breeders is to develop high-yielding hybrids that are agronomically sound based on stable inbred lines. The reasons for this goal are obvious: to maximize the amount of marketable dent corn produced with the inputs used and minimize susceptibility of the crop to pests and environmental stresses.

To accomplish this goal, the breeder must select and develop superior inbred parental lines for producing hybrids. This requires identification and selection of genetically unique individuals that occur in a segregating population. The segregating population is the result of a combination of crossover events plus the independent assortment of specific combinations of alleles at many gene loci that results in specific genotypes. The probability of selecting any one individual with a specific genotype from a breeding cross is very low due to the large number of segregating genes and the unlimited recombinations of these genes, some of which may be closely linked. However, the genetic variation among individual progeny of a breeding cross allows for the identification of rare and valuable new genotypes. These new genotypes are neither predictable nor incremental in value, but rather the result of manifested genetic variation combined with selection methods, environments and the actions of the breeder.

Thus, even if the entire genotypes of the parents of the breeding cross were characterized and a desired genotype known, only a few, if any, individuals having the desired genotype may be found in a large segregating F2 population. Typically, however, neither the genotypes of the breeding cross parents nor the desired genotype to be selected is known in any detail. In addition, it is not known how the desired genotype would react with the environment. This genotype by environment interaction is an important, yet unpredictable, factor in plant breeding. A breeder of ordinary skill in the art cannot predict the genotype, how that genotype will interact with various climatic conditions or the resulting phenotypes of the developing lines, except perhaps in a very broad and general fashion. A breeder of ordinary skill in the art would also be unable to recreate the same line twice from the very same original parents as the breeder is unable to direct how the genomes combine or how they will interact with the environmental conditions. This unpredictability results in the expenditure of large amounts of research resources in the development of a superior new maize inbred line, such as a superior new sweet corn inbred line.

Inbred maize lines, such as inbred corn lines, are typically developed for use in the production of hybrid maize lines, for example hybrid dent corn lines. Inbred maize lines need to be highly homogeneous, homozygous and reproducible to be useful as parents of commercial hybrids. There are many analytical methods available to determine the homozygotic and phenotypic stability of these inbred lines. The oldest and most traditional method of analysis is the observation of phenotypic traits. The data is usually collected in field experiments over the life of the maize plants to be examined. Phenotypic characteristics often observed are for traits associated with plant morphology, ear and kernel morphology, insect and disease resistance, maturity, and yield.

In addition to phenotypic observations, a plant can also be identified by its genotype. The genotype of a plant can be characterized through a genetic marker profile.

As a result of inbreeding, I10516 is substantially homozygous. This homozygosity can be characterized at the loci shown in a marker profile. An F1 hybrid made with I10516 would substantially comprise the marker profile of I10516. This is because an F1 hybrid is the sum of its inbred parents, e.g., if one inbred parent is homozygous for allele x at a particular locus, and the other inbred parent is homozygous for allele y at that locus, the F1 hybrid will be x.y (heterozygous) at that locus. A genetic marker profile can therefore be used to identify hybrids comprising I10516 as a parent, since such hybrids will comprise two sets of alleles, one set of which will be from I10516. The determination of the male set of alleles and the female set of alleles may be made by profiling the hybrid and the pericarp of the hybrid seed, which is composed of maternal parent cells. One way to obtain the paternal parent profile is to subtract the pericarp profile from the hybrid profile.

Subsequent generations of progeny produced by selection and breeding are expected to be of genotype xx (homozygous), yy (homozygous), or xy (heterozygous) for these locus positions. When the F1 plant is used to produce an inbred, the resulting inbred should be either x or y for that allele.

Therefore, in accordance with the above, an embodiment of this invention is a I10516 progeny maize plant or plant part that is a first generation (F1) hybrid maize plant comprising two sets of alleles, wherein one set of the alleles is the same as I10516 at substantially all loci. A maize cell wherein one set of the alleles is the same as I10516 at substantially all loci is also an embodiment of the invention. This maize cell may be a part of a hybrid seed, plant or plant part produced by crossing I10516 with another maize plant.

Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don et al., "Assessing Probability of Ancestry Using Simple Sequence Repeat Profiles: Applications to Maize Hybrids and Inbreds", Genetics, 2002, 161:813-824, and Berry, Don et al., "Assessing Probability of Ancestry Using Simple Sequence Repeat Profiles: Applications to Maize Inbred Lines and Soybean Varieties", Genetics, 2003, 165: 331-342.

Particular markers used for these purposes are not limited to the set of markers disclosed herein, but may include any type of marker and marker profile which provides a means of distinguishing varieties. In addition to being used for identification of maize variety I10516, a hybrid produced through the use of I10516, and the identification or verification of pedigree for progeny plants produced through the use of I10516, a genetic marker profile is also useful in developing a locus conversion of I10516.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

I10516 and its plant parts can be identified through a molecular marker profile. Such plant parts may be either diploid or haploid. Also encompassed within the scope of the invention are plants and plant parts substantially benefiting from the use of I10516 in their development, such as I10516 comprising a locus conversion.

Comparing I10516 to Other Inbreds

A breeder uses various methods to help determine which plants should be selected from segregating populations and ultimately which inbred varieties will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred varieties and hybrid combinations are significantly better or different for one or more traits of interest. Experimental design methods are used to assess error so that differences between two inbred varieties or two hybrid varieties can be more accurately evaluated. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is a significant difference between the two traits expressed by those varieties. For example, see Fehr, Walt, Principles of Cultivar Development, p. 261-286 (1987). Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide tolerance, insect or disease resistance. A locus conversion of I10516 for herbicide tolerance should be compared with an isogenic counterpart in the absence of the converted trait. In addition, a locus conversion for insect or disease resistance should be compared to the isogenic counterpart, in the absence of disease pressure or insect pressure.

Development of Maize Hybrids Using I10516

A single cross maize hybrid results from the cross of two inbred varieties, each of which has a genotype that complements the genotype of the other. A hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased yield.

I10516 may be used to produce hybrid maize. One such embodiment is the method of crossing maize variety I10516 with another maize plant, such as a different maize variety, to form a first generation F1 hybrid seed. The first generation F1 hybrid seed, plant and plant part produced by this method is an embodiment of the invention. The first generation F1 seed, plant and plant part will comprise an essentially complete set of the alleles of variety I10516. One of ordinary skill in the art can utilize molecular methods to identify a particular F1 hybrid plant produced using variety I10516. Further, one of ordinary skill in the art may also produce F1 hybrids with transgenic, male sterile and/or locus conversions of variety I10516.

The development of a maize hybrid in a maize plant breeding program involves three steps: (1) the selection of plants from various germplasm pools for initial breeding crosses; (2) the selfing of the selected plants from the breeding crosses for several generations to produce a series of varieties, such as I10516, which, although different from each other, breed true and are highly uniform; and (3) crossing the selected varieties with different varieties to produce the hybrids. During the inbreeding process in maize, the vigor of the varieties decreases, and so one would not be likely to use I10516 directly to produce grain. However, vigor is restored when I10516 is crossed to a different inbred variety to produce a commercial F1 hybrid. An important consequence of the homozygosity and homogeneity of the inbred variety is that the hybrid between a defined pair of inbreds may be reproduced indefinitely as long as the homogeneity of the inbred parents is maintained.

I10516 may be used to produce a single cross hybrid, a double cross hybrid, or a three-way hybrid. A single cross hybrid is produced when two inbred varieties are crossed to produce the F1 progeny. A double cross hybrid is produced from four inbred varieties crossed in pairs (A×B and C×D) and then the two F1 hybrids are crossed again (A×B)×(C×D). A three-way cross hybrid is produced from three inbred varieties where two of the inbred varieties are crossed (A×B) and then the resulting F1 hybrid is crossed with the third inbred (A×B)×C. In each case, pericarp tissue from the female parent will be a part of and protect the hybrid seed.

Molecular data from I10516 may be used in a plant breeding process. Nucleic acids may be isolated from a seed of I10516 or from a plant, plant part, or cell produced by growing a seed of I10516, or from a seed of I10516 with a locus conversion, or from a plant, plant part, or cell of I10516 with a locus conversion. One or more polymorphisms may be isolated from the nucleic acids. A plant having one or more of the identified polymorphisms may be selected and used in a plant breeding method to produce another plant.

Combining Ability of I10516

Combining ability of a variety, as well as the performance of the variety per se, is a factor in the selection of improved maize inbreds. Combining ability refers to a variety's contribution as a parent when crossed with other varieties to form hybrids. The hybrids formed for the purpose of selecting superior varieties may be referred to as test crosses, and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the varieties.

General combining ability provides an overall score for the inbred over a large number of test crosses. Specific combining ability provides information on hybrid combinations formed by I10516 and a specific inbred parent. A variety such as I10516 which exhibits good general combining ability may be used in a large number of hybrid combinations.

The general combining ability and hybrid comparisons for I10516 is provided in Tables 2-4.

Hybrid Comparisons

The hybrid comparisons shown in Tables 2-4 represent specific hybrid crosses with I10516 and comparisons of these specific hybrids with other hybrids with favorable characteristics. These comparisons illustrate the good specific combining ability of I10516. The results in Tables 2-4 compare a specific hybrid for which I10516 is a parent with other hybrids. The data in Tables 2-4 show that numerous species of the genus of F1 hybrids created with I10516 have been reduced to practice. These comparisons illustrate the good specific combining ability of I10516.

Locus Conversions of I10516

I10516 represents anew base genetic variety into which a new locus may be introgressed. Direct transformation and backcrossing represent two important methods that can be used to accomplish such an introgression. The term locus conversion is used to designate the product of such an introgression.

A locus conversion of I10516 will retain the genetic integrity of I10516. A locus conversion of I10516 will comprise at least 90%, 91%, 92%, 93%, 94%, 95%, 96%, 97%, 98% or 99% of the genetic identity of I10516 as determined by using SSR markers or SNP markers. For example, a locus conversion of I10516 can be developed when DNA sequences are introduced through backcrossing (Hallauer et al. in Corn and Corn Improvement, Sprague and Dudley, Third Ed. 1998), with I10516 utilized as the recurrent parent. Both naturally occurring and transgenic DNA sequences may be introduced through backcrossing techniques. A backcross conversion may produce a plant with a trait or locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding, In: Proceedings Symposium of the Analysis of Molecular Data, August 1994, Crop Science Society of America, Corvallis, Oreg., where it is demonstrated that a locus conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single locus traits that are relatively easy to classify, the backcross method is effective and relatively easy to manage. (See Hallauer et al. in Corn and Corn Improvement, Sprague and Dudley, Third Ed. 1998). Desired traits that may be transferred through locus conversion include, but are not limited to, waxy starch, sterility (nuclear and cytoplasmic), fertility restoration, grain color (white), nutritional enhancements, drought resistance, enhanced nitrogen utilization efficiency, altered nitrogen responsiveness, altered fatty acid profile, increased digestibility, low phytate, industrial enhancements, disease resistance (bacterial, fungal or viral), insect resistance, herbicide tolerance and yield enhancements. A locus conversion, also called a trait conversion, can be a native trait or a transgenic trait. In addition, an introgression site itself, such as an FRT site, Lox site or other site specific integration site, may be inserted by backcrossing and utilized for direct insertion of one or more genes of interest into a specific plant variety.

The seed industry commonly markets "triple stacks" of base genetics; which can be varieties comprising a locus conversion of at least 3 loci. Similarly, "quadruple stacks" would comprise the base genetics and could comprise a locus conversion of at least 4 loci. A single locus may contain several transgenes, such as a transgene for disease resistance that, in the same expression vector, also contains a transgene for herbicide tolerance. As used herein, the phrase 'comprising a' transgene, transgenic event or locus conversion means one or more transgenes, transgenic events or locus conversions. The gene for herbicide tolerance may be used as a selectable marker and/or as a phenotypic trait. A locus conversion of a site specific integration system allows for the integration of multiple genes at the converted loci. Further, SSI and FRT technologies known to those of skill in the art in the art may result in multiple gene introgressions at a single locus.

The locus conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype and/or genotype of the recurrent parent. While occasionally additional polynucleotide sequences or genes may be transferred along with the backcross conversion, the backcross conversion variety "fits into the same hybrid combination as the recurrent parent inbred variety and contributes the effect of the additional locus added through the backcross." ((Poehlman et al (1995) *Breeding Field Crop*, 4th Ed., Iowa State University Press, Ames, Iowa, pp. 132-155 and 321-344)). When one or more traits are introgressed into the variety a difference in quantitative agronomic traits, such as yield or dry down, between the variety and an introgressed version of the variety in some environments may occur. For example, the introgressed version may provide a net yield increase in environments where the trait provides a benefit, such as when a variety with an introgressed trait for insect resistance is grown in an environment where insect pressure exists, or when a variety with herbicide tolerance is grown in an environment where herbicide is used.

One process for adding or modifying a trait or locus in maize variety I10516 comprises crossing I10516 plants grown from I10516 seed with plants of another maize variety that comprise the desired trait or locus, selecting F1 progeny plants that comprise the desired trait or locus to produce selected F1 progeny plants, crossing the selected progeny plants with the I10516 plants to produce backcross progeny plants, selecting for backcross progeny plants that have the desired trait or locus and the phenotypic characteristics of maize variety I10516 to produce selected backcross progeny plants; and backcrossing to I10516 one or more times in succession to produce backcross progeny plants that comprise said trait or locus. The modified I10516 may be further characterized as having essentially the same phenotypic characteristics of maize variety I10516 listed in Table 1 and/or may be characterized by percent identity to I10516 as determined by molecular markers, such as SSR markers or SNP markers.

In addition, the above process and other similar processes described herein may be used to produce F1 hybrid maize seed by adding a step at the end of the process that comprises crossing I10516 with the locus conversion with a different maize plant and harvesting the resultant F1 hybrid maize seed.

Traits are also used by those of ordinary skill in the art to characterize progeny. Traits are commonly evaluated at a significance level, such as a 1%, 5% or 10% significance level, when measured in plants grown in the same environmental conditions.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production.

I10516 can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile designated I10516 may include one or more genetic factors, which result in cytoplasmic genetic and/or nuclear genetic male sterility. All of such embodiments are within the scope of the present claims. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown. CMS systems have been successfully used since the 1950's, and the male sterility trait is routinely backcrossed into inbred varieties. See Wych, Robert D. (1988) "Production of Hybrid Seed", Corn and Corn Improvement, Ch. 9, pp. 565-607.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describes a system of nuclear male sterility which includes identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These, and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et al. EPO 89/3010153.8 publication no. 329,308 and PCT application PCT/CA90/00037 published as WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., and U.S. Pat. No. 4,936,904). Application of the gametocide, timing of the application and genotype specificity often limit the usefulness of the approach and it is not appropriate in all situations.

Incomplete control over male fertility may result in self-pollinated seed being unintentionally harvested and packaged with hybrid seed. This would typically be only female parent seed, because the male plant is grown in rows that are typically destroyed prior to seed development. Once the seed from the hybrid bag is planted, it is possible to identify and select these self-pollinated plants. These self-pollinated plants will be one of the inbred varieties used to produce the hybrid. Though the possibility of I10516 being included in a hybrid seed bag exists, the occurrence is very low because much care is taken by seed companies to avoid such inclusions. It is worth noting that hybrid seed is sold to growers for the production of grain or forage and not for breeding or seed production. These self-pollinated plants can be identified and selected by one skilled in the art due to their less vigorous appearance for vegetative and/or reproductive characteristics, including shorter plant height, small ear size, ear and kernel shape, or other characteristics.

Identification of these self-pollinated varieties can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, 1-8 (1995), the disclosure of which is expressly incorporated herein by reference. Through these technologies, the homozygosity of the self-pollinated variety can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

Transformation

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are stably inserted into the cell using transformation are referred to herein collectively as "trans-genes" and/or "transgenic events". In some embodiments of the invention, a transformed variant of I10516 may comprise at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transformed versions of the claimed maize variety I10516 as well as hybrid combinations thereof.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been stably engineered into the germ cell line of a particular maize plant using transformation techniques, could be moved into the germ cell line of another variety using traditional breeding techniques that are well known in the plant breeding arts. For example, a backcrossing approach is commonly used to move a transgenic event from a transformed maize plant to another variety, and the resulting progeny would then comprise the transgenic event(s). Also, if an inbred variety was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953, which are herein incorporated by reference. In addition, transformability of a variety can be increased by introgressing the trait of high transformability from another variety known to have high transformability, such as Hi-II. See U.S. Patent Application Publication US2004/0016030 (2004).

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114: 92-6 (1981).

Transgenic events can be mapped by one of ordinary skill in the art and such techniques are well known to those of ordinary skill in the art. For exemplary methodologies in this regard, see for example, Glick and Thompson, Methods in Plant Molecular Biology and Biotechnology 269-284 (CRC Press, Boca Raton, 1993).

Likewise, by means of the present invention, plants can be genetically engineered to express various phenotypes of agronomic interest. Through the transformation of maize the expression of genes can be altered to enhance disease resistance, insect resistance, herbicide tolerance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* Ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) *Plant Cell* 9: 1245; Jorgensen (1990) *Trends Biotech.* 8(12):340-344; Flavell (1994) *PNAS* USA 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS* USA 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) Plant Cell 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089(1994) (*Arabidopsis* RSP2 gene for resistance to *Pseudomonas syringae*), McDowell & Woffenden, (2003) Trends Bio-technol. 21(4): 178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 7,105,332; 7,208,474; WO 91/14778; WO 99/31248; WO 01/12731; WO 99/24581; WO 97/40162 and U.S. application Ser. Nos. 10/032,717; 10/414,637; 11/018,615; 11/404,297; 11/404,638; 11/471,878; 11/780,501; 11/780,511; 11/780,503; 11/953,648; 11/953,648; and Ser. No. 11/957,893.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269:9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7):847-853; and Vasconcelos & Oliveira (2004) Toxicon 44 (4): 40 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, and U.S. Pat. Nos. 6,563,020; 7,145,060 and 7,087,810.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 and U.S. Pat. No. 5,580,852 disclosure of peptide derivatives of Tachyplesin which inhibit fungal plant pathogens and PCT application WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., Nature 366: 469 (1993), which shows that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995), Pieterse & Van Loon (2004) Curr. Opin. Plant Bio. 7(4):456-64 and Somssich (2003) *Cell* 113(7):815-6.

(P) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. Nos. 09/950,933; 11/619,645; 11/657,710; 11/748,994; 11/774,121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716,820; 5,792,931; 5,798,255; 5,846,812; 6,083,736; 6,538,177; 6,388,171 and 6,812,380.

(R) Cystatin and cysteine proteinase inhibitors. See U.S. Pat. No. 7,205,453.

(S) Defensin genes. See WO03000863 and U.S. Pat. Nos. 6,911,577; 6,855,865; 6,777,592 and 7,238,781.

(T) Genes conferring resistance to nematodes. See e.g. PCT Application WO96/30517; PCT Application WO93/19181, WO 03/033651 and Urwin et al., Planta 204:472-479 (1998), Williamson (1999) Curr. Opin. Plant Bio. 2(4):327-31; and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent publication US20090035765 and incorporated by reference for this purpose. This includes the Rcg locus that may be utilized as a single locus conversion.

(X) A lectin. See, for example, the article by Van Damme et al., *Plant Molec. Biol.* 24:25 (1994), who disclose the nucleotide sequences of several *Clivia miniata* mannose-binding lectin genes.

(Y) A vitamin-binding protein such as avidin. See PCT application US93/06487. The application teaches the use of avidin and avidin homologues as larvicides against insect pests.

2. Transgenes That Confer Tolerance To An Herbicide, For Example:

(A) An herbicide that inhibits the growing point or meristem, such as an imidazolinone or a sulfonylurea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively. See also, U.S. Pat. Nos. 5,605,011; 5,013,659; 5,141,870; 5,767,361; 5,731,180; 5,304,732; 30 4,761,373; 5,331,107; 5,928,937; and 5,378,824; U.S. application Ser. No. 11/683,737, and international publication WO 96/33270.

(B) Glyphosate (tolerance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy propriionic acids and cyclohexones (ACCase inhibitor-encoding genes). See, for example, U.S. Pat. No. 4,940,835 to Shah et al., which discloses the nucleotide sequence of a form of EPSPS which can confer glyphosate tolerance. U.S. Pat. No. 5,627,061 to Barry et al. also describes genes encoding EPSPS enzymes. See also U.S. Pat. Nos. 6,566,587; 6,338,961; 6,248,876 B1; U.S. Pat. Nos. 6,040,497; 5,804,425; 5,633,435; 5,145,783; 4,971,908; 5,312,910; 5,188,642; 4,940,835; 5,866,775; 6,225,114 B1; U.S. Pat. Nos. 6,130,366; 5,310,667; 4,535,060; 4,769,061; 5,633,448; 5,510,471; RE 36,449; RE 37,287 E; and 5,491,288; and international publications EP1173580; WO 01/66704; EP1173581 and EP1173582, which are incorporated herein by reference for this purpose. Glyphosate tolerance is also imparted to plants that express a gene that encodes a glyphosate oxidoreductase enzyme as described more fully in U.S. Pat. Nos. 5,776,760 and 5,463,175, which are incorporated herein by reference for this purpose. In addition glyphosate tolerance can be imparted to plants by the over expression of genes encoding glyphosate N-acetyltransferase. See, for example, U.S. application Ser. Nos. 10/427,692; 10/835,615 and 11/507,751. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer tolerance to herbicides such as L-phosphinothricin. The nucleotide sequence of a phosphinothricin-acetyltransferase gene is provided in European Patent No. 0 242 246 and 0 242 236 to Leemans et al.

De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall et al., *Theor. Appl. Genet.* 83: 435 (1992).

(C) An herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol. Gen. Genet. 246: 419). Other genes that confer tolerance to herbicides include: a gene encoding a chimeric protein of rat cytochrome P4507A1 and yeast NADPH-cytochrome P450 oxidoreductase (Shiota et al. (1994) Plant Physiol 106:17), genes for glutathione reductase and superoxide dismutase (Aono et al. (1995) Plant Cell Physiol 36:1687), and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are tolerant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such as:

(A) Altered fatty acids, for example, by:

(1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superal1, milps, various Ipa genes such as Ipa1, Ipa3, hpt or hggt. For example, see WO 02/42424, WO 98/22604, WO 03/011015, WO 02/057439, WO 03/011015, U.S. Pat. Nos. 6,423,886, 6,197,561, 6,825,397, and U.S. Application Publication Nos. US2003/0079247, US2003/0204870, and Rivera-Madrid, R. et al. Proc. Natl. Acad. Sci. 92:5620-5624 (1995).

(B) Altered phosphorus content, for example, by the (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) Modulating a gene that reduces phytate content. In maize, this, for example, could be accomplished by cloning and then re-introducing DNA associated with one or more of the alleles, such as the LPA alleles, identified in maize mutants characterized by low levels of phytic acid, such as in WO 05/113778 and/or by altering inositol kinase activity as in WO 02/059324, US2003/0009011, WO 03/027243, US2003/0079247, WO 99/05298, U.S. Pat. No. 6,197,561, U.S. Pat. No. 6,291,224, U.S. Pat. No. 6,391,348, WO 2002/059324, US2003/0079247, WO 98/45448, WO 99/55882, WO 01/04147.

(C) Altered carbohydrates affected, for example, by altering a gene for an enzyme that affects the branching pattern of starch or, a gene altering thioredoxin such as NTR and/or TRX (see. (See U.S. Pat. No. 6,531,648 which is incorporated by reference for this purpose) and/or a gamma zein knock out or mutant such as cs27 or TUSC27 or en27 (See U.S. Pat. No. 6,858,778 and US2005/0160488, US2005/0204418; which are incorporated by reference for this purpose). See Shiroza et al., J. Bacterial. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Molec. Biol. 21:515 (1993) (nucleotide sequences of tomato invertase genes), Søgaard et al., J. Biol. Chem. 268:22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 99/40209 (alteration of amino acid compositions in seeds), WO 99/29882 (methods for altering amino acid content of proteins), U.S. Pat. No. 5,850,016 (alteration of amino acid compositions in seeds), WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO 98/45458 (engineered seed protein having higher percentage of essential amino acids), WO 98/42831

(increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 96/01905 (increased threonine), WO 95/15392 (increased lysine), US2003/0163838, US2003/0150014, US2004/0068767, U.S. Pat. No. 6,803, 498, WO 01/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al., Plant Mol. Biol. 19:611-622, 1992).

For additional examples of nuclear male and female sterility systems and genes, see also, U.S. Pat. Nos. 5,859, 341; 6,297,426; 5,478,369; 5,824,524; 5,850,014; and 6,265,640 all of which are hereby incorporated by reference.

5. Genes that create a site for site specific DNA integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, *The Maize Handbook* Ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress.

For example, see: WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; 6,801,104; WO2000060089; WO2001026459; WO2001035725; WO2001034726; WO2001035727; WO2001036444; WO2001036597; WO2001036598; WO2002015675; WO2002017430; WO2002077185; WO2002079403; WO2003013227; WO2003013228; WO2003014327; WO2004031349; WO2004076638; WO9809521; and WO9938977 describing genes, including CBF genes and transcription factors effective in mitigating the negative effects of freezing, high salinity, and drought on plants, as well as conferring other positive effects on plant phenotype; US2004/0148654 and WO 01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. No. 6,177,275, and U.S. Pat. No. 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), WO2004076638 and WO2004031349 (transcription factors).

Expression Vectors for Corn Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which, when placed under the control of plant regulatory signals, confers resistance to kanamycin (Fraley et al., *Proc. Natl. Acad. Sci. U.S.A.*, 80:4803 (1983)). Another commonly used selectable marker gene is the hygromycin phosphotransferase gene which confers resistance to the antibiotic hygromycin (Vanden Elzen et al., *Plant Mol. Biol.*, 5:299 (1985)).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., *Plant Physiol.* 86:1216 (1988), Jones et al., *Mol. Gen. Genet.*, 210:86 (1987), Svab et al., *Plant Mol. Biol.* 14:197 (1990), and Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), and Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), beta-galactosidase, luciferase, and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), and DeBlock et al., *EMBO J.* 3:1681 (1984). Another approach to the identification of relatively rare transformation events has been use of a gene that encodes a dominant constitutive regulator of the *Zea mays* anthocyanin pigmentation pathway (Ludwig et al., *Science* 247:449 (1990)).

In vivo methods for visualizing GUS activity that do not require destruction of plant tissue are also available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells (Chalfie et al., *Science* 263:802 (1994)). GFP and mutants of GFP may be used as screenable markers.

Expression Vectors for Corn Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain organs, such as leaves, roots, seeds and tissues such as fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent. Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. U.S.A.* 90:4567-4571 (1993)); In2 gene from maize which responds to benzenesulfonamide herbicide safeners (Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in corn or the constitutive promoter is operably linked to a nucleotide sequence encoding a signal sequence which is operably linked to a gene for expression in corn. Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231: 276-285 (1992) and Atanassova et al., *Plant Journal* 2 (3): 291-300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-specific or Tissue-preferred Promoters—A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), Stiefel, et al., *Plant Cell* 2:785-793 (1990).

Using I10516 to Develop Another Maize Plant

Maize varieties such as I10516 are typically developed for use in the production of hybrid maize varieties. However, varieties such as I10516 also provide a source of breeding material that may be used to develop new maize inbred varieties. Plant breeding techniques known in the art and used in a maize plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred varieties, the crossing of these varieties, and the evaluation of the crosses. There are many analytical methods available to evaluate the result of a cross. The oldest and most traditional method of analysis is the observation of phenotypic traits, but genotypic analysis may also be used.

This invention is also directed to methods for producing a maize plant by crossing a first parent maize plant with a second parent maize plant wherein either the first or second parent maize plant is a maize plant of the variety I10516. The other parent may be any other maize plant, such as another inbred variety or a plant that is part of a synthetic or natural population. Any such methods using the maize variety I10516 are part of this invention: selfing, sibbing, backcrosses, mass selection, pedigree breeding, bulk selection hybrid production, crosses to populations, and the like. These methods are well known in the art and some of the more commonly used breeding methods are described below. Descriptions of breeding methods can also be found in one of several reference books (e.g., Allard, *Principles of Plant Breeding*, 1960; Simmonds, *Principles of Crop Improvement*, 1979; Fehr, "Breeding Methods for Cultivar Development", *Production and Uses*, $2^{nd}$ ed., Wilcox editor, 1987, the disclosure of which is incorporated herein by reference).

Pedigree Breeding

Pedigree breeding starts with the crossing of two genotypes, such as I10516 and one other inbred variety having one or more desirable characteristics that is lacking or which complements I10516. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: F1→F2; F2→F3; F3→F4; F4→F5, etc. After a sufficient amount of inbreeding, successive filial generations will serve to increase seed of the developed inbred. Preferably, the inbred variety comprises homozygous alleles at about 95% or more of its loci.

Recurrent Selection and Mass Selection

Recurrent selection is a method used in a plant breeding program to improve a population of plants. I10516 is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and toperossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred varieties to be used in hybrids or used as parents for a synthetic cultivar. A synthetic cultivar is the resultant progeny formed by the intercrossing of several selected inbreds.

I10516 is suitable for use in mass selection. Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self-pollination, directed pollination could be used as part of the breeding program.

Mutation Breeding

Mutation breeding is one of many methods that could be used to introduce new traits into I10516. I10516 is suitable for use in a mutation breeding program. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993 Macmillan Publishing Company, the disclosure of which is incorporated herein by reference. In addition, mutations created in other varieties may be used to produce a backcross conversion of 10 I10516 that comprises such mutation.

Production of Double Haploids

The production of double haploids can also be used for the development of inbreds in the breeding program. For example, an F1 hybrid for which I10516 is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and US2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected variety (as female) with an inducer variety. Such inducer varieties for maize include Stock 6 (Coe, 1959, *Am. Nat.* 93:381-382; Sharkar and Coe, 1966, *Genetics* 54:453-464) RWS (see world wide web site www.uni-hohenheim.deP/07Eipspwww/350b/indexe.html#Project3), KEMS (Deimling, Roeber, and Geiger, 1997, *Vortr. Pflanzenzuchtg* 38:203-224), KMS and ZMS (Chalyk, Bylich & Chebotar, 1994, *MNL* 68:47; Chalyk & Chebotar, 2000, *Plant Breeding* 119:363-364), and indeterminate gametophyte (ig) mutation (Kermicle 1969 *Science* 166:1422-1424). The disclosures of which are incorporated herein by reference.

Methods for obtaining haploid plants are also disclosed in Kobayashi, M. et al., *Journ. of Heredity* 71(1):9-14, 1980, Pollacsek, M., Agronomie (Paris) 12(3):247-251, 1992; Cho-Un-Haing et al., *Journ. of Plant Biol.*, 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, *Maize Genet. Coop. Newsletter* 73:53-54; Coe, R. H., 1959, *Am. Nat.* 93:381-382; Deimling, S. et al., 1997, *Vortr. Pflanzenzuchtg* 38:203-204; Kato, A., 1999, J. Hered. 90:276-280; Lashermes, P. et al., 1988, *Theor. Appl. Genet.* 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, *Indian J. Genet Plant Breed* 38:452-457; Chalyk S. T., 1994, Euphytica 79:13-18; Chase, S. S., 1952, *Agron. J.* 44:263-267; Coe, E. H., 1959, Am. Nat. 93:381-382; Coe, E. H., and Sarkar, K. R., 1964 *J. Hered.* 55:231-233; Greenblatt, I. M. and Bock, M., 1967, *J. Hered.* 58:9-13; 60 Kato, A., 1990, Maize Genet. Coop. Newsletter 65:109-110; Kato, A., 1997, *Sex. Plant Reprod.* 10:96-100; Nanda, D. K. and Chase, S. S., 1966, *Crop Sci.* 6:213-215; Sarkar, K. R. and Coe, E. H., 1966, *Genetics* 54:453-464; Sarkar, K. R. and Coe, E. H., 1971, *Crop Sci.* 11:543-544; Sarkar, K. R. and Sachan J. K. S., 1972, *Indian J. Agric. Sci.* 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; U.S. Pat. No. 5,639,951 and U.S. patent application Ser. No. 10/121,200, the disclosures of which are incorporated herein by reference.

Thus, an embodiment of this invention is a process for making a homozygous I10516 progeny plant substantially similar to I10516 by producing or obtaining a seed from the cross of I10516 and another maize plant and applying double haploid methods to the F1 seed or F1 plant or to any successive filial generation. Such methods decrease the number of generations required to produce an inbred with similar genetics or characteristics to I10516. See Bernardo, R. and Kahler, A. L., *Theor. Appl. Genet.* 102:986-992, 2001.

In particular, a process of making seed substantially retaining the molecular marker profile of maize variety I10516 is contemplated, such process comprising obtaining or producing F1 hybrid seed for which maize variety I10516 is a parent, inducing double haploids to create progeny without the occurrence of meiotic segregation, obtaining the molecular marker profile of maize variety I10516, and selecting progeny that retain the molecular marker profile of I10516.

Another embodiment of the invention is a maize seed derived from inbred maize variety I10516 produced by crossing a plant or plant part of inbred maize variety I10516 with another plant, wherein representative seed of said inbred maize variety I10516 has been deposited and wherein said maize seed derived from the inbred maize variety I10516 has 92%, 93%, 94%, 95%, 96%, 97%, 98% or 99% of the same polymorphisms for molecular markers as the plant or plant part of inbred maize variety I10516. The number of molecular markers used for the molecular marker profile can be the 161 public markers, the sequences for which can be found in the Panzea database which is located at the World Wide Web panzea.org. The type of molecular marker used in the molecular profile can be but is not limited to SingleNucleotide Polymorphisms, SNPs. A maize seed derived from inbred maize variety I10516 produced by crossing a plant or plant part of inbred maize variety I10516 with another plant, wherein representative seed of said inbred maize variety I10516 has been deposited and wherein said maize seed derived from the inbred maize variety I10516 has essentially the same morphological characteristics as maize variety I10516 when grow in the same environmental conditions. The same environmental conditions may be, but is not limited to a side-by-side comparison. The characteristics can be those listed in Table 1. The comparison can be made using any number of professionally accepted experimental designs and statistical analysis.

Use of I10516 in Tissue Culture

This invention is also directed to the use of I10516 in tissue culture. As used herein, the term "tissue culture" includes plant protoplasts, plant cell tissue culture, cultured microspores, plant calli, plant clumps, and the like. As used herein, phrases such as "growing the seed" or "grown from the seed" include embryo rescue, isolation of cells from seed for use in tissue culture, as well as traditional growing methods.

Duncan, Williams, Zehr, and Widhalm, Planta (1985) 165: 322-332 reflects that 97% of the plants cultured that produced callus were capable of plant regeneration. Subsequent experiments with both inbreds and hybrids produced 91% regenerable callus that produced plants. In a further study in 1988, Songstad, Duncan & Widhalm in *Plant Cell Reports* (1988), 7:262-265 reports several media additions that enhance regenerability of callus of two inbred varieties.

Other published reports also indicated that "nontraditional" tissues are capable of producing somatic embryogenesis and plant regeneration. K. P. Rao, et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize, including tassel/anther culture, is described in U.S. 2002/0062506A1 and European Patent Application, publication EP0160,390, each of which are incorporated herein by reference for this purpose. Maize tissue culture procedures are also described in Green and Rhodes, "Plant Regeneration in Tissue Culture of Maize," *Maize for Biological Research* (Plant Molecular Biology Association, Charlottesville, Va. 1982, at 367-372) and in Duncan, et al., "The Production of Callus Capable of Plant Regeneration from Immature Embryos of Numerous *Zea Mays* Genotypes," 165 *Planta* 322-332 (1985). Thus, another aspect of this invention is to provide cells which upon growth and differentiation produce maize plants having the genotype and/or phenotypic characteristics of variety I10516.

Seed Treatments and Cleaning

Another embodiment of this invention is the method of harvesting the seed of the maize variety I10516 as seed for planting. Embodiments include cleaning the seed, treating the seed, and/or conditioning the seed. Cleaning the seed includes removing foreign debris such as weed seed and removing chaff, plant matter, from the seed. Conditioning the seed can include controlling the temperature and rate of dry down and storing seed in a controlled temperature environment. Seed treatment is the application of a composition to the seed such as a coating or powder. Some examples of compositions are insecticides, fungicides, pesticides, antimicrobials, germination inhibitors, germination promoters, cytokinins, and nutrients.

To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, *azospirillum*, azadirachtin, azoxystrobin, *bacillus* spp. (including one or more of *cereus, firmus, megaterium, pumilis, sphaericus, subtilis* and/or *thuringiensis*), *bradyrhizobium* spp. (including one or more of *betae, canariense, elkanii, iriomotense, japonicum, liaonigense, pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

In one embodiment, seeds of inbred corn line I10516 or seeds of inbred corn plants of I10516 further comprising one or more single gene traits are provided as an essentially homogeneous population of inbred corn seeds. Essentially homogeneous populations of inbred seed are those that consist essentially of the particular inbred seed, and are generally purified free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 100% of inbred seed, as measured by seed grow outs. The population of inbred corn seeds of the invention is further particularly defined as being essentially free from hybrid seed. Thus, one particular embodiment of this invention is isolated inbred seed of inbred corn plants of I10516, e.g., substantially free from hybrid seed or seed of other inbred seed, e.g., a seed lot or unit of inbred seed which is at least 95% homogeneous. The inbred seed population may be separately grown to provide an essentially homogeneous population of plants of inbred corn line I10516 or inbred corn plants of I10516 further comprising one or more single gene traits.

Seeds of inbred corn plants of I10516 for planting purposes is preferably containerized, e.g., placed in a bag or other container for ease of handling and transport and is preferably coated, e.g., with protective agents, e.g., safening or pesticidal agents, in particular antifungal agents and/or insecticidal agents.

When inbred corn line I10516 is identified herein, it is understood that the named line include varieties which have the same genotypic and phenotypic characteristics as the identified varieties, i.e., are derived from a common inbred source, even if differently named.

The present invention provides a genetic complement of the corn plant variety designated I10516. As used herein, the phrase "genetic complement" means an aggregate of nucleotide sequences, the expression of which defines the phenotype of a corn plant or a cell or tissue of that plant. By way of example, a corn plant is genotyped to determine a representative sample of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence or size of a repeated sequence. Heterozygosity refers to different conditions of the gene at a locus. A preferred type of genetic marker for use with the invention is simple sequence repeats (SSRs), although potentially any other type of genetic marker could be used, for example, restriction fragment length polymorphisms (RFLPs), amplified fragment length polymorphisms (AFLPs), single nucleotide polymorphisms (SNPs), and isozymes.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

Industrial Applicability

Another embodiment of this invention is the method of harvesting the grain of the F1 plant of variety I10516 and using the grain in a commodity, such as a commodity plant product. Examples of maize grain as a commodity include but are not limited to oils, meals, flour, starches, syrups, proteins, and sugars. Maize grain is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of maize variety I10516, the plant produced from the seed, the hybrid maize plant produced from the crossing of the variety, hybrid seed, and various parts of the hybrid maize plant and transgenic versions of the foregoing, can be utilized for human food, livestock feed, and as a raw material in industry.

Table(s)

Inbred corn line I10516 has been used as a parent to create new corn hybrids. For example, corn hybrids EX1, EX2, and EX3 all have inbred corn line I10516 as a parent. Tables 2-4 show the results of trials planted in numerous locations throughout Ohio, Indiana, Kentucky and Illinois from 2013-2015 comparing corn hybrids EX1, EX2 and EX3 to commercial corn hybrids. The results show the mean values across all trials. In Table 2, corn hybrid EX1, which has inbred corn line I10516 as a parent, is compared to commercial corn hybrids Phoenix® 5726A4, BECK 5385A3, XL® 6543HR™, Phoenix® 5552EZ, XL® 6175AMXT™, XL® 6272AM™, XL® 6575HR™ and Phoenix® 5842EZ. The entire data set can also be viewed as comparing I10516 hybrids with other, related commercial hybrids. Table 2, column 1 shows the number of years tested, column 2 shows the hybrid designation, column 3 shows the number of comparisons, column 4 shows the yield in bushels/acre (bu/a), column 5 shows the percent water (% H2O) and column 6 shows the test weight in pounds/bushel (lbs/bu).

TABLE 2

| Number of years | Hybrid | Number of comparisons | Yield (bu/a) | % H$_2$O | Test weight (lbs/bu) |
|---|---|---|---|---|---|
| 1 | EX1 | 76 | 219.2 | 21.6 | |
| 1 | Phoenix ® 5726A4 | 76 | 213.6 | 21.8 | |
| 2 | EX1 | 113 | 218.3 | 21.7 | 57.5 |
| 2 | BECK 5385A3 | 113 | 212.4 | 20.5 | 57.1 |
| 2 | EX1 | 190 | 219.1 | 21.6 | 57.5 |
| 2 | XL ® 6543HR ™ | 190 | 217.7 | 22.3 | 57.6 |
| 2 | EX1 | 162 | 220.0 | 21.5 | 57.5 |
| 2 | Phoenix ® 5552EZ | 162 | 213.2 | 21.0 | 55.8 |
| 2 | EX1 | 239 | 215.3 | 21.1 | 57.9 |
| 2 | XL ® 6175AMXT ™ | 239 | 210.9 | 21.1 | 58.3 |
| 2 | EX1 | 220 | 213.4 | 21.0 | 57.9 |
| 2 | XL ® 6272AM ™ | 220 | 207.1 | 21.1 | 58.8 |
| 3 | EX1 | 117 | 221.3 | 21.1 | 58.1 |
| 3 | XL ® 6575HR ™ | 117 | 219.5 | 22.9 | 57.7 |
| 3 | EX1 | 266 | 215.3 | 21.3 | 57.9 |
| 3 | Phoenix ® 5842EZ | 266 | 210.4 | 20.9 | 56.6 |

Table 3 shows the results when corn hybrid EX2, which has inbred corn line I10516 as a parent, is compared to commercial corn hybrids BECK 5385A3, XL® 6543HR™, XL® 5475AM™ Phoenix® 5552EZ™, XL® 6175AMXT™, and XL® 6575HR™. In Table 3, column 1 shows the number of years tested, column 2 shows the hybrid designation, column 3 shows the number of comparisons, column 4 shows the yield in bushels/acre (bu/a), column 5 shows the percent water (% H2O) and column 6 shows the test weight in pounds/bushel (lbs/bu).

TABLE 3

| Number of years | Hybrid | Number of comparisons | Yield (bu/a) | % H$_2$O | Test weight (lbs/bu) |
| --- | --- | --- | --- | --- | --- |
| 1 | EX2 | 128 | 214.9 | 22.3 | 57.5 |
| 1 | BECK 5385A3 | 128 | 212.6 | 20.1 | 57.2 |
| 2 | EX2 | 219 | 220.3 | 22.0 | 57.6 |
| 2 | XL ® 6543HR ™ | 219 | 219.4 | 22.2 | 58.4 |
| 2 | EX2 | 24 | 239.1 | 19.7 | 60.4 |
| 2 | XL ® 5475AM ™ | 24 | 216.4 | 18.5 | 60.8 |
| 1 | EX2 | 132 | 216.8 | 22.4 | 57.6 |
| 1 | Phoenix ® 5552EZ ™ | 132 | 212.1 | 21.0 | 56.2 |
| 1 | EX2 | 181 | 222.5 | 22.7 | 57.3 |
| 1 | XL ® 6175AMXT ™ | 181 | 219.0 | 21.6 | 58.3 |
| 2 | EX2 | 152 | 228.9 | 21.3 | 58.7 |
| 2 | XL ® 6575HR ™ | 152 | 223.1 | 23.0 | 58.4 |

Table 4 shows the results when corn hybrid EX3, which has inbred corn line I10516 as a parent, is compared to commercial corn hybrids Phoenix® 5552EZ™, XL® 6175AMXT™, XL® 5131AM™, XL® 5475AMXT™, XL® 6272AM™, Phoenix® 5842EZ™ and XL® 5939AMXT™. In Table 4, column 1 shows the number of years tested, column 2 shows the hybrid designation, column 3 shows the number of comparisons, column 4 shows the yield in bushels/acre (bu/a), column 5 shows the percent water (% H2O) and column 6 shows the test weight in pounds/bushel (lbs/bu).

TABLE 4

| Number of years | Hybrid | Number of comparisons | Yield (bu/a) | % H$_2$O | Test weight (lbs/bu) |
| --- | --- | --- | --- | --- | --- |
| 2 | EX3 | 14 | 212.2 | 17.9 | 59.8 |
| 2 | Phoenix ® 5552EZ ™ | 14 | 199.7 | 18.0 | 56.6 |
| 1 | EX3 | 120 | 207.6 | 20.3 | 58.0 |
| 1 | XL ® 6175AMXT ™ | 120 | 205.2 | 20.3 | 58.8 |
| 1 | EX3 | 21 | 194.2 | 17.9 | 58.9 |
| 1 | XL ® 5131AM ™ | 21 | 182.8 | 16.6 | 58.1 |
| 1 | EX3 | 41 | 210.0 | 19.0 | 58.3 |
| 1 | XL ® 5475AMXT ™ | 41 | 197.3 | 17.5 | 59.7 |
| 2 | EX3 | 152 | 202.3 | 19.8 | 58.2 |
| 2 | XL ® 6272AM ™ | 152 | 200.9 | 19.7 | 59.5 |
| 2 | EX3 | 83 | 207.4 | 20.7 | 58.1 |
| 2 | Phoenix ® 5842EZ ™ | 83 | 201.3 | 20.2 | 57.1 |
| 2 | EX3 | 126 | 208.5 | 20.2 | 58.0 |
| 2 | XL ® 5939AMXT ™ | 126 | 205.9 | 19.3 | 58.2 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the Beck's Superior Hybrids proprietary INBRED CORN LINE I10516 disclosed above and recited in the appended claims has been made with the American Type Culture Collection (ATCC), 10801 University Boulevard, Manassas, Va. 20110 under the terms of the Budapest Treaty. The date of deposit was May 13, 2016. The deposit of 2,500 seeds was taken from the same deposit maintained by Beck's Superior Hybrids since prior to the filing date of this application. All restrictions will be irrevocably removed upon granting of a patent, and the deposit is intended to meet all of the requirements of 37 C.F.R. §§1.801-1.809. The ATCC Accession Number is PTA-123122. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed, plant, plant part, or cell of inbred corn line I10516, wherein a representative sample of seed of said inbred corn line was deposited under ATCC Accession No. PTA-123122.

2. A method comprising isolating nucleic acids from the seed, plant, plant part, or cell of claim 1.

3. An F$_1$ hybrid corn seed produced by crossing the plant or plant part of claim 1 with a different corn plant.

4. An F$_1$ hybrid corn plant produced by growing the corn seed of claim 3.

5. A method for producing a second corn plant comprising applying plant breeding techniques to a first corn plant, or parts thereof, wherein said first corn plant is the F$_1$ hybrid corn plant of claim 4, and wherein application of said techniques results in the production of said second corn plant.

6. The method of claim 5, comprising:
   (a) crossing said first corn plant with itself or another corn plant to produce seed of a subsequent generation;
   (b) harvesting and planting the seed of the subsequent generation to produce at least one plant of the subsequent generation; and
   (c) repeating steps (a) and (b) for an additional 2-10 generations to produce the second corn plant.

7. The second corn plant produced by the method of claim 6, wherein said second corn plant has all of the morphological and physiological characteristics listed in Table 1 of inbred corn line I10516 when grown in the same environmental conditions.

8. The method of claim 5, comprising:
(a) crossing said first corn plant with an inducer variety to produce haploid seed; and
(b) doubling the haploid seed to produce the second corn plant.

9. The second corn plant produced by the method of claim 8, wherein said second corn plant has all of the morphological and physiological characteristics listed in Table 1 of inbred corn line I10516 when grown in the same environmental conditions.

10. A seed, plant, plant part, or cell of inbred corn line I10516, representative seed of said variety having been deposited under ATCC accession number PTA-123122, further comprising a locus conversion, wherein said seed, plant, plant part, or cell otherwise has all of the morphological and physiological characteristics listed in Table 1 of inbred corn line I10516 when grown in the same environmental conditions.

11. The seed, plant, plant part, or cell of claim 10, wherein the locus conversion confers a trait selected from the group consisting of male sterility, site-specific recombination, abiotic stress tolerance, altered phosphorus, altered antioxidants, altered fatty acids, altered essential amino acids, altered carbohydrates, herbicide tolerance, insect resistance and disease resistance.

12. A method comprising isolating nucleic acids from the converted seed, converted plant, plant part, or cell of claim 10.

13. An $F_1$ hybrid corn seed produced by crossing the plant or plant part of claim 10 with a different corn plant.

14. An $F_1$ hybrid corn plant produced by growing the seed of claim 13.

15. A method for producing a second corn plant comprising applying plant breeding techniques to a first corn plant, or parts thereof, wherein said first corn plant is the $F_1$ hybrid corn plant of claim 14, and wherein application of said techniques results in production of said second corn plant.

16. The method of claim 15, comprising:
(a) crossing said first corn plant with itself or another corn plant to produce seed of a subsequent generation;
(b) harvesting and planting the seed of the subsequent generation to produce at least one plant of the subsequent generation; and
(c) repeating steps (a) and (b) for an additional 2-10 generations to produce the second corn plant.

17. The second corn plant produced by the method of claim 16, wherein said second corn plant has all of the morphological and physiological characteristics listed in Table 1 of inbred corn line I10516 when grown under the same environmental conditions.

18. The method of claim 15, comprising:
(a) crossing said first corn plant with an inducer variety to produce haploid seed; and
(b) doubling the haploid seed to produce the second corn plant.

19. The second corn plant produced by the method of claim 18, wherein said second corn plant has all of the morphological and physiological characteristics listed in Table 1 of inbred corn line I10516 when grown under the same environmental conditions.

20. A method of producing a commodity plant product, comprising obtaining the plant of claim 1, or a part thereof, and producing the commodity plant product from said plant or plant part thereof, wherein said commodity plant product is selected from the group consisting of livestock feed, starch, ethanol, biomass, oil, meal, flour, syrup, protein, sugar, grits, dextrose, germ, biofuel and refined chemicals.

21. The commodity plant product produced by the method of claim 20, wherein the commodity plant product comprises at least one cell of inbred corn line I10516.

\* \* \* \* \*